US012329217B2

(12) United States Patent
Simmons

(10) Patent No.: US 12,329,217 B2
(45) Date of Patent: Jun. 17, 2025

(54) STRESS TEST GARMENT AND METHOD OF USE

(71) Applicant: Innovation Ventures IP at UKHS, LLC., Westwood, KS (US)

(72) Inventor: Ashley Simmons, Westwood, KS (US)

(73) Assignee: Innovation Ventures IP at UKHS, LLC., Westwood, KS (US)

( * ) Notice: Subject to any disclaimer, the term of this patent is extended or adjusted under 35 U.S.C. 154(b) by 1030 days.

(21) Appl. No.: 16/013,411

(22) Filed: Jun. 20, 2018

(65) Prior Publication Data

US 2018/0368495 A1 Dec. 27, 2018

Related U.S. Application Data

(60) Provisional application No. 62/522,462, filed on Jun. 20, 2017.

(51) Int. Cl.
*A61B 5/05* (2021.01)
*A41C 3/00* (2006.01)
(Continued)

(52) U.S. Cl.
CPC ........ *A41D 13/1281* (2013.01); *A41C 3/0057* (2013.01); *A41C 3/0064* (2013.01);
(Continued)

(58) Field of Classification Search
CPC ..... A61B 5/282; A61B 5/6804; A61B 5/0006; A61B 5/25; A61B 5/318; A61B 5/6805; A61B 5/6823; A61B 5/0245; A61B 5/0024; A61B 5/6831; A61B 5/7203; A61B 5/1118; A61B 2562/164; A61B 5/6833;
(Continued)

(56) References Cited

U.S. PATENT DOCUMENTS 4,608,987 A * 9/1986 Mills ................ A61B 5/282
600/389
5,327,888 A 7/1994 Imran
(Continued)

FOREIGN PATENT DOCUMENTS

EP 3245948 A1 11/2017
WO 2008092098 A2 7/2008
(Continued)

OTHER PUBLICATIONS

"Signal Processing" at https://www.signal-processing.com/table.php on Mar. 24, 2017 (scan made available via the WayBack Machine archive) (Year: 2017).*
(Continued)

*Primary Examiner* — Joseph A Stoklosa
*Assistant Examiner* — Brian M Antiskay
(74) *Attorney, Agent, or Firm* — Polsinelli PC

(57) ABSTRACT

The disclosed invention relates generally to various embodiments of garments for use with electrocardiographs. In particular, the invention relates to a garment with a lead placement layer or precordial patch with incorporated ECG leads and a support layer configured to support the breasts of a user while a patient undergoes an exercise stress electrocardiograph. Various portions of the garment are easily and quickly removable.

15 Claims, 10 Drawing Sheets

(51) Int. Cl.
  *A41D 13/12* (2006.01)
  *A61B 5/00* (2006.01)
  *A61B 5/22* (2006.01)
  *A61B 5/282* (2021.01)
  *A61B 5/30* (2021.01)
  *A61B 5/349* (2021.01)
  *A61B 5/0205* (2006.01)

(52) U.S. Cl.
  CPC .......... *A41D 13/1245* (2013.01); *A61B 5/222* (2013.01); *A61B 5/282* (2021.01); *A61B 5/303* (2021.01); *A61B 5/349* (2021.01); *A61B 5/4884* (2013.01); *A61B 5/6804* (2013.01); *A61B 5/6823* (2013.01); *A61B 5/02055* (2013.01); *A61B 2503/10* (2013.01); *A61B 2505/09* (2013.01); *A61B 2562/222* (2013.01)

(58) Field of Classification Search
  CPC ..... A61B 5/024; A61B 5/259; A61B 2503/10; A61B 5/6869; A61N 1/0484; A61N 1/3925; A61N 1/3904; A61N 1/0476; A61N 1/0492
  USPC .......................... 600/372, 382–393, 508–509
  See application file for complete search history.

(56) References Cited

U.S. PATENT DOCUMENTS

| | | | | |
|---|---|---|---|---|
| 5,445,149 | A | * | 8/1995 | Rotolo .................. A61B 5/6831 |
| | | | | 600/382 |
| 5,458,141 | A | | 10/1995 | Neil |
| 5,678,545 | A | | 10/1997 | Stratbucker |
| 5,868,671 | A | | 2/1999 | Mahoney |
| 5,965,809 | A | | 10/1999 | Pechter |
| 6,006,125 | A | | 12/1999 | Kelly et al. |
| 6,023,785 | A | | 2/2000 | Johnson |
| 6,141,575 | A | | 10/2000 | Price |
| 6,360,119 | B1 | | 3/2002 | Roberts |
| 6,847,836 | B1 | | 1/2005 | Sujdak |
| 8,224,418 | B2 | | 7/2012 | Birnbaum et al. |
| 8,626,260 | B2 | | 1/2014 | Crosby |
| 8,954,129 | B1 | | 2/2015 | Schlegel et al. |
| 9,277,867 | B2 | | 3/2016 | Kurzweil et al. |
| 2004/0226069 | A1 | | 11/2004 | Reeves |
| 2005/0251004 | A1 | | 11/2005 | Istvan et al. |
| 2008/0077217 | A1 | | 3/2008 | Santamore et al. |
| 2008/0154110 | A1 | | 6/2008 | Burnes et al. |
| 2008/0177168 | A1 | | 7/2008 | Callahan et al. |
| 2008/0287769 | A1 | | 11/2008 | Kurzweil et al. |
| 2009/0258572 | A1 | * | 10/2009 | Chayo .................. A41F 15/002 |
| | | | | 450/86 |
| 2010/0160763 | A1 | * | 6/2010 | Tsai ...................... A61B 5/6831 |
| | | | | 600/393 |
| 2011/0004088 | A1 | | 1/2011 | Grossman |
| 2012/0122370 | A1 | * | 5/2012 | Heath .................. A41C 3/0057 |
| | | | | 450/80 |
| 2012/0283794 | A1 | | 11/2012 | Kaib et al. |
| 2013/0053674 | A1 | | 2/2013 | Volker |
| 2013/0281795 | A1 | | 10/2013 | Varadan |
| 2013/0281815 | A1 | | 10/2013 | Varadan |
| 2014/0012145 | A1 | | 1/2014 | Kurzweil et al. |
| 2015/0305677 | A1 | * | 10/2015 | Berg ....................... A61B 5/24 |
| | | | | 600/388 |
| 2016/0066809 | A1 | | 3/2016 | Luo et al. |
| 2016/0256104 | A1 | | 9/2016 | Romem et al. |
| 2016/0310075 | A1 | | 10/2016 | Ross et al. |
| 2017/0100046 | A1 | | 4/2017 | Roh et al. |

FOREIGN PATENT DOCUMENTS

| | | |
|---|---|---|
| WO | 2016114298 A1 | 7/2016 |
| WO | 2017075703 A1 | 5/2017 |

OTHER PUBLICATIONS

Halpern, E.J., et al. "A Novel Approach to Reduce Breast Radiation Exposure with Coronary CTA," Academic Radiology, 2009, 16(8):951-956.
Extended European Search Report for EP 18819563.0 dated Mar. 3, 2021, 12 pages.
International Search Report and Written Opinion for PCT/US2018/038532 dated Jun. 20, 2018, 9 pages.
European Patent Office, Communication pursuant to Article 94(3), Application No. 18819563.0, dated Jan. 19, 2023, 7 pages.
European Patent Office, Communication Pursuant to Article 94(3) EPC, Application No. 18819563.0, dated Jun. 21, 2022, 5 pages.

* cited by examiner

STRESS TEST GARMENT AND METHOD OF USE

BACKGROUND

Cardiovascular disease is the leading cause of death in women and affects 1 in 3 women in the United States. To help diagnosis and treatment of cardiovascular disease, one common method is an exercise stress electrocardiogram, which is a noninvasive screening test, used to evaluate for coronary artery disease. With an exercise stress electrocardiogram, the physician can measure exercise capacity, electrocardiographic changes of ischemia and also evaluate if symptoms of chest pain or shortness of breath correspond with ischemic electrocardiographic changes. The EKG or ECG test is sometimes commonly referred to as a "stress test" or "treadmill test". The overall test checks for changes in your heart that are monitored with an ECG machine and is often combined with imaging, either an echocardiogram or nuclear imaging, conducted immediately after conclusion of the exercise portion of the test. It has been found that the exercise capacity on an exercise stress electrocardiogram is an independent predictor of heart health conditions and potential death in women. The St James Women Take Heart Project showed that the Framingham Risk Score adjusted mortality risk decreased by 17% for every 1-MET increase (metabolic equivalent).

Because of the importance of the "stress test," or exercise electrocardiogram, it is imperative that the initial step of placement of electrode leads for electrocardiograms is correct to ensure accurate diagnosis of ischemic changes in women. Ensuring proper placement of the ECG leads in women can be difficult, oftentimes, because the anterior lateral leads are placed under the breasts too low and can cause artifact or cause interpretation errors on the electrocardiogram. Improper placement of the leads can be further magnified when the women begins to exercise, since the vertical and horizontal breast displacement can cause electrocardiographic artifact making interpretation of the stress electrocardiogram difficult.

The exercise component of the stress test evaluates for ischemic changes of the heart while under stress. Exercise stress tests, particularly exercise stress echocardiograms are currently performed without breast support in place, which can be uncomfortable for a woman since breast tissue has limited anatomical support. The skin covering the breast tissue and fibrous thin bands of tissue, called Cooper's ligaments, are the only anatomic structures that support breast tissue. Due to the limited anatomical support of breast tissue, external support is recommended. This is best accomplished with breast compression and elevation which have been shown to decrease exercise induced breast discomfort.

Excessive vertical breast tissue displacement is associated with exercise induced breast discomfort and embarrassment in women. Many large breasted women refrain from physical activity due to the pain and/or embarrassment associated with excessive breast motion. Breast discomfort has been shown to impact exercise participation in younger women. In a study in the UK, 96% of girls aged 11-18 wore breast support and 46% of girls reported that their breasts had an effect on their participation in sports and exercise. Breast discomfort has been found to directly correlate with breast size. Because breast size in the United States is increasing, bra manufacturers have reported that the average bra size has increased from a 34 B to a 34 DD over the last 20 years in America, the problems associated with the exercise component of the stress test will only increase.

For a typical exercise electrocardiogram test it is recommended that a woman perform the exercise portion without breast support, such as a bra or other under garment in place so not to inhibit lead placement or imaging. If a woman is required to complete the exercise without any support garment it is highly likely she will experience discomfort and possibly embarrassment that could lead to her hesitation to take the test or to not perform the exercise at maximum exertion. One of the reasons for conducting the test without an under garment is to ensure that when the imagining of the heart is conducted, at the end of the exercise portion, that the garment does not distort the image or inhibit image acquisition of the heart. It could be possible for women to remove a garment, however the best images are taken of the active heart directly after the exercise and any delay of image acquisition, even if minimal, can interfere with the tests' accuracy.

Therefore, a need exists for a garment that allows for correct electrocardiographic lead placement and for the rapid access by a sonographer to accurately image the heart or for image acquisition with nuclear stress testing immediately following the exercise portion of the stress test. The desired garment will provide compression and support for various sizes of breasts, further includes integrated placement of standard multi-lead ECG leads, allows a medical professional to easily place the garment on the women and will allow a woman to perform an exercise electrocardiogram test with the leads properly in place. The garment will also limit vertical breast motion, decrease electrocardiographic attenuation, and improve comfort in a woman undergoing the exercise stress testing portion. The garment will further include a layer that is composed of material that will allow for radiolucent and echolucent imaging without complete removal of the garment, while a certain portion of the garment is removed for stress echocardiogram to allow rapid image acquisition.

SUMMARY

The purpose of this disclosure is to provide a garment assembly for use with an electrocardiogram. The assembly may include a lead placement layer, a support layer, and an array of electrocardiographic electrodes for use with electrocardiogram analysis. The support layer may have the form of a sports bra. Additionally, the support layer may have some of the same functions as a sports bra, namely supporting a user's breast while exercising. In some embodiments, a body portion of the support layer may have two ends that are detachedly affixed to one another. These ends may be detachedly affixed to one another using traditional bra clasps, a tri-glide, a hook and loop fastener, or combinations thereof.

Because the assembly may be used with exercise stress testing which may include electrocardiogram, nuclear cardiology imaging, and echocardiogram, the components of the assembly may be formed from radiolucent materials. In some embodiments the components of the assembly are formed from echolucent materials. Additionally, the support layer may be configured for quick removal so the chest of the patient can be easily accessed. In this regard, the support layer may include at least one strap that has a fastener configured for holding at least one free end of the body portion of the support layer in order to keep the body portion from obstructing access and view of the patient's chest.

In some embodiments the lead placement layer is configured to be removably attached to the skin of a patient. In this regard, the lead placement layer may include an adhesive on at least one surface. The lead placement layer may be fixedly attached, removeably attached, or not attached to the support layer. Additionally, the lead placement layer may have other attributes that are advantageous for use while exercising. In some embodiments, the lead placement layer may remain sticky or adherent in the presence of sweat or other fluids. The lead placement layer may also provide moisture wicking capabilities in order to remove moisture from a patient's skin. Similarly, the support layer may also be configured to wick sweat away from the patient.

The garment assembly may be used by a method comprising the steps of measuring the chest size of a patient, choosing a lead placement layer that corresponds to the chest size of the patient, choosing a support layer that corresponds to the chest size of the patient, placing the lead placement layer on the patient, connecting the lead placement layer to an electrocardiogram monitor, placing the support layer on the patient, disconnecting the assembly from an electrocardiogram monitor, and removing the garment. In an embodiment, the method may include the step of connecting a free end of support layer to a strap of the support layer.

The assembly may be part of a system for determining a lead placement layer and a support layer using the chest size of a patient. The system may comprise, determining the patient's bra size, using the bra size to determine the appropriate size of lead placement layer and support layer. In some embodiments the size of the lead placement layer may be determined by using a circumference of the patient's chest. In some embodiments the size of the support layer is determined by using a circumference of the patient's chest.

DETAILED DESCRIPTION

Figure 1:
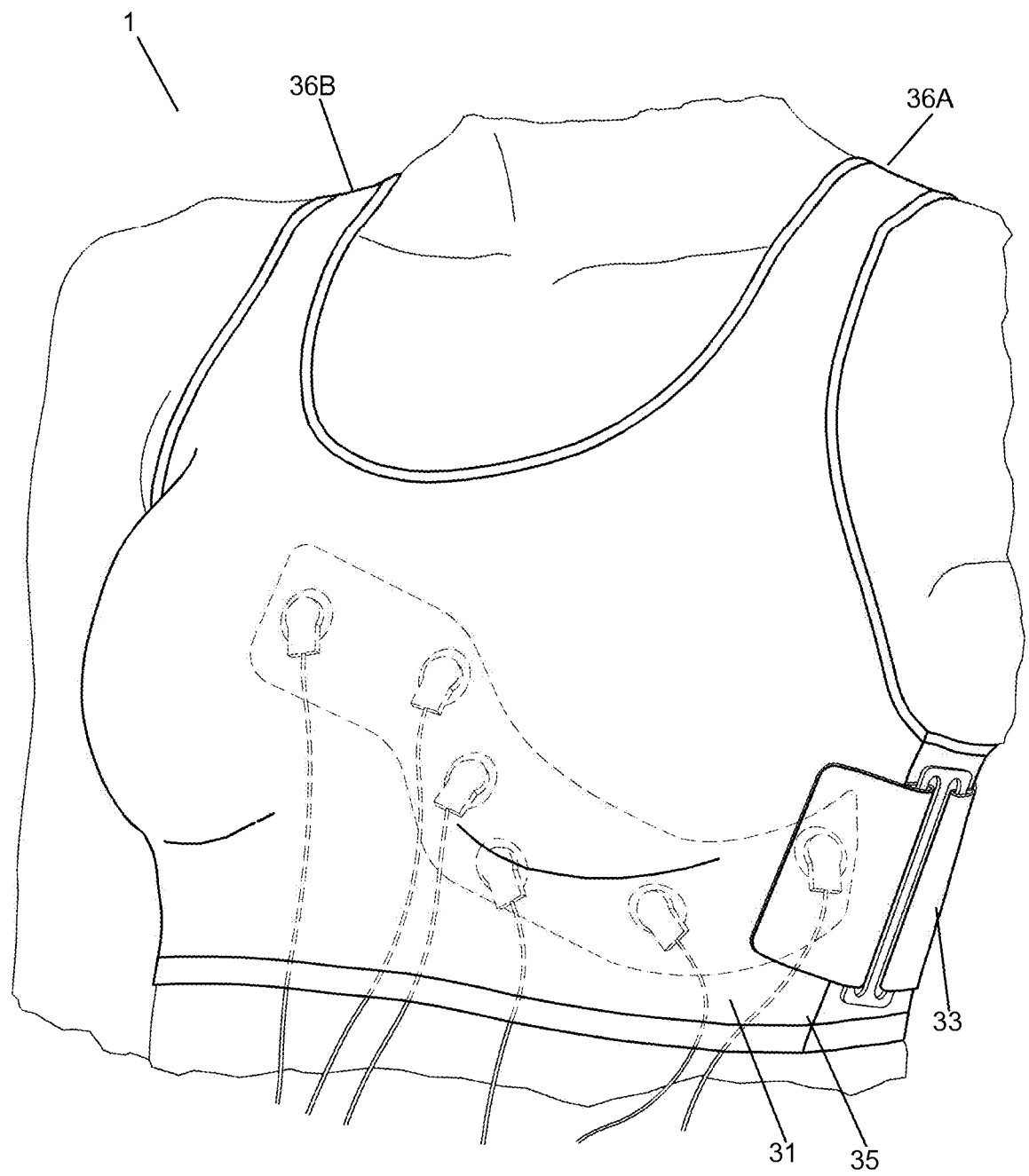
FIG. 1 is a view of the torso wearing a stress test garment.
Figure 2:
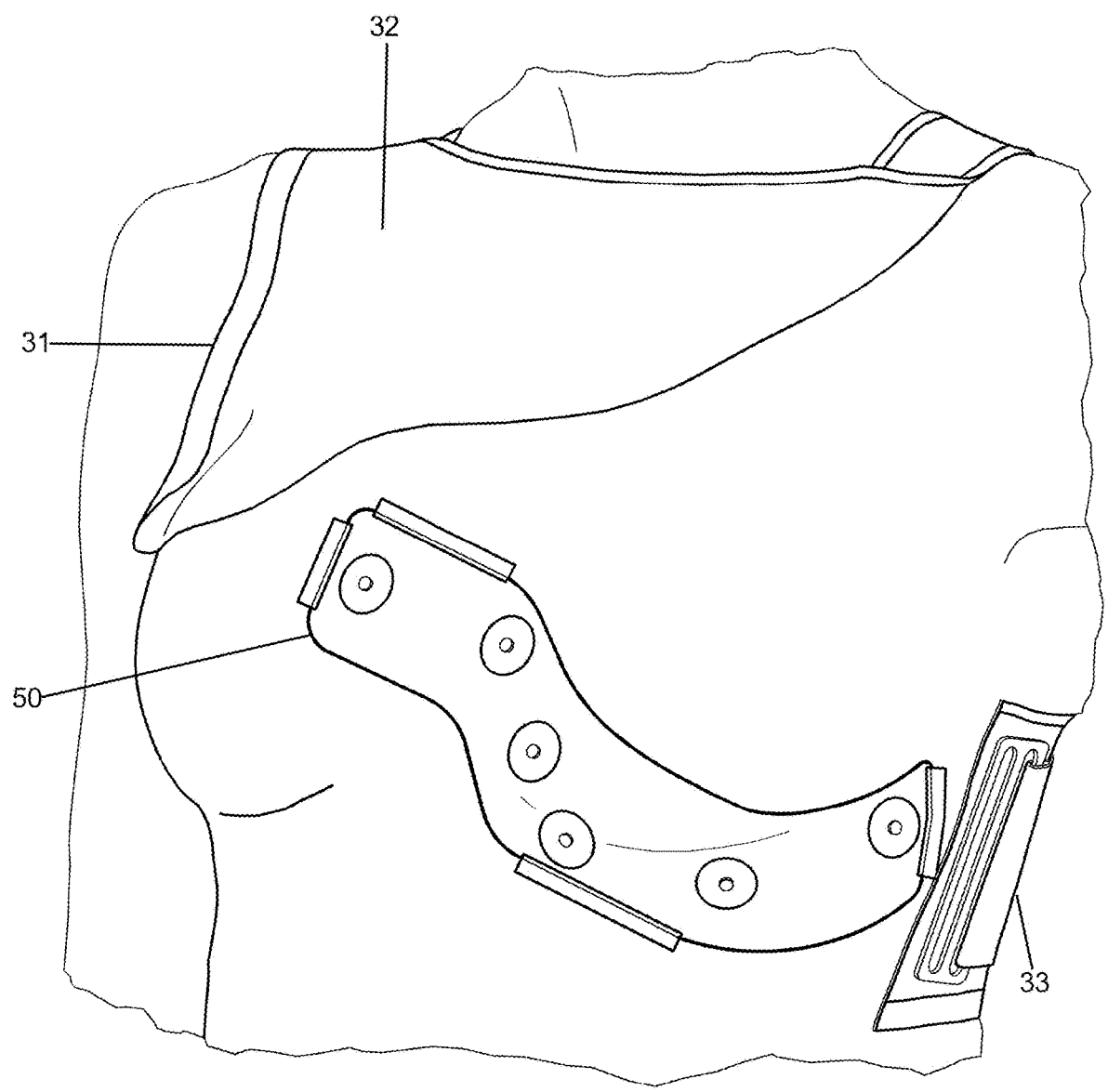
FIG. 2 is a view of the stress test garment with the support layer raised.
Figure 3:
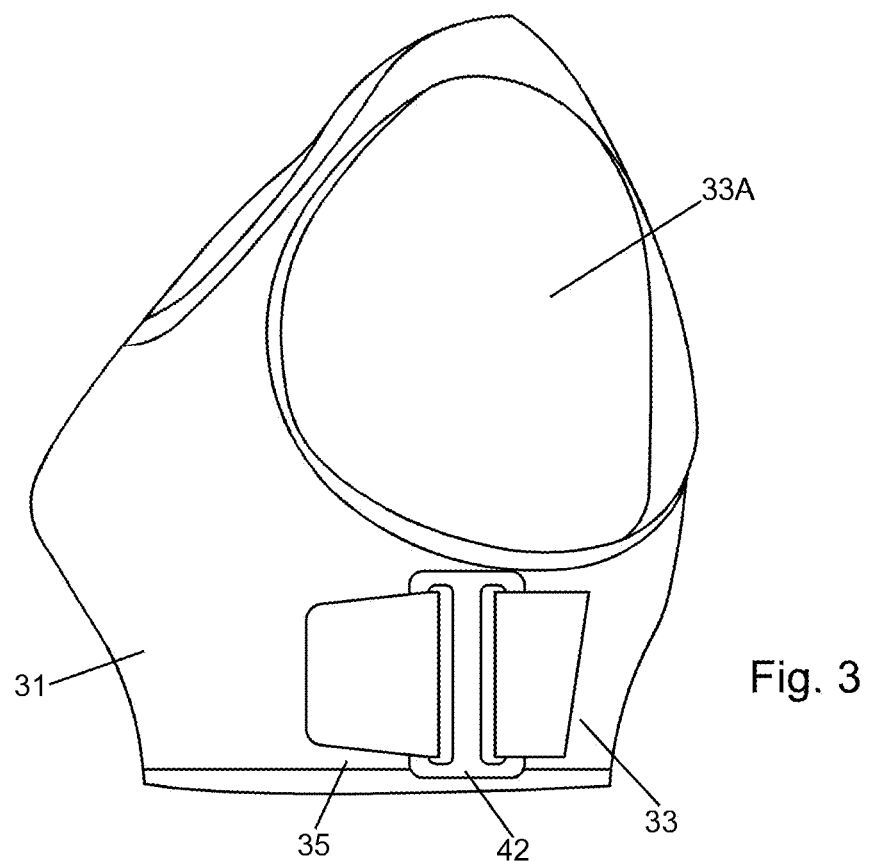
FIG. 3 is a side view of the stress test garment.
Figure 4:
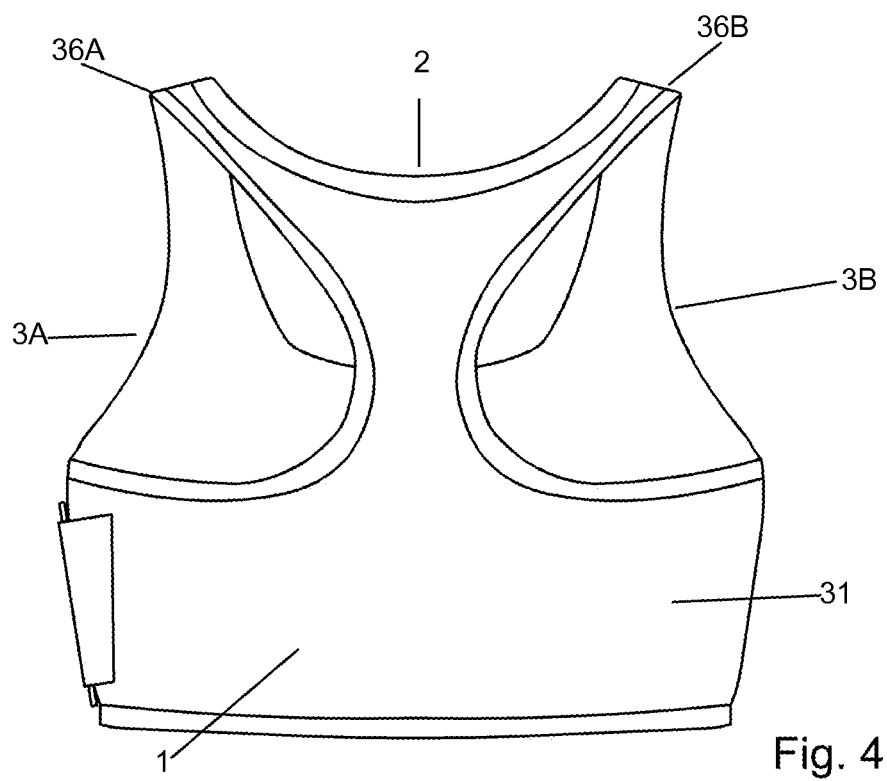
FIG. 4 is a rear view of the stress test garment.

This invention relates generally to a stress test garment. The garment 1 is configured for use in exercise electrocardiogram testing or stress testing with ECG lead placements configured with the lead placement layer fixedly attached, removably attached or not attached to the support layer 30 that allows a medical professional to easily place the ECG leads in proper formation on the user. More particularly the invention is to a garment configured with integrated ECG leads or a multi-lead ECG patch (precordial patch) for use with the garment that will also provide support for the breasts during exercise but allows for rapid removal of any materials that could inhibit imaging during testing. The garment 1 will assist with lead placement, in particular on a woman, and minimize lead artifact induced by breast motion. The garment 1 may also include material integrated into the design that are both echolucent and radiolucent to reduce artifacts when the chest is imaged using various methods including nuclear imaging and echocardiographic imaging.

In one embodiment, the garment 1 will be configured with two layers, a first internal lead placement layer 10 having leads disposed and strategically placed within the first layer, and a second support layer 30 that is configured to provide the desired support for the breasts of the user, such as found in traditional undergarments used during exercise. In an alternate embodiment, the garment 1 will further include a precordial patch 50 (multi-lead ECG patch) that works in conjunction with lead placement layer 10 where the lead placement layer 10 or support layer 30 will include indicia 24 that aligns with the placement of the precordial patch 50 to ensure the proper lead placement on the patient. In another embodiment, the garment 1 may include a precordial patch 50 but not a lead placement layer 10. The lead placement layer 10 configured as a precordial patch 50 can be fixedly attached, removably attached or not attached to the support layer 30. Where the precordial patch 50 is attached to the patient and the support layer 30 then covers the precordial patch 50 to hold the patients' breasts in place during the exercise portion of any tests.

Figure 7:
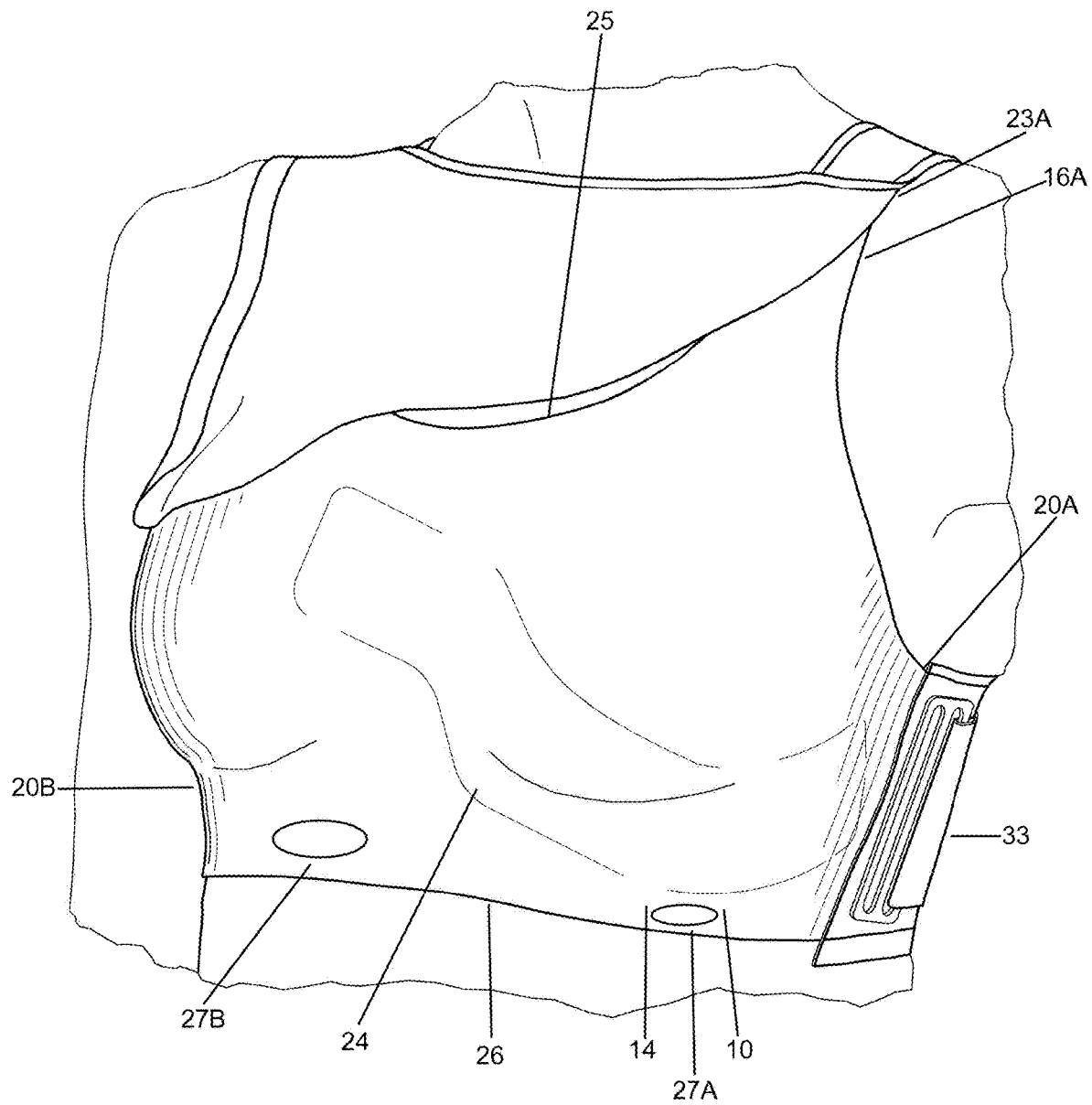
FIG. 7 is view of an embodiment of the stress test garment with a lead placement layer and support layer.
Figure 8:
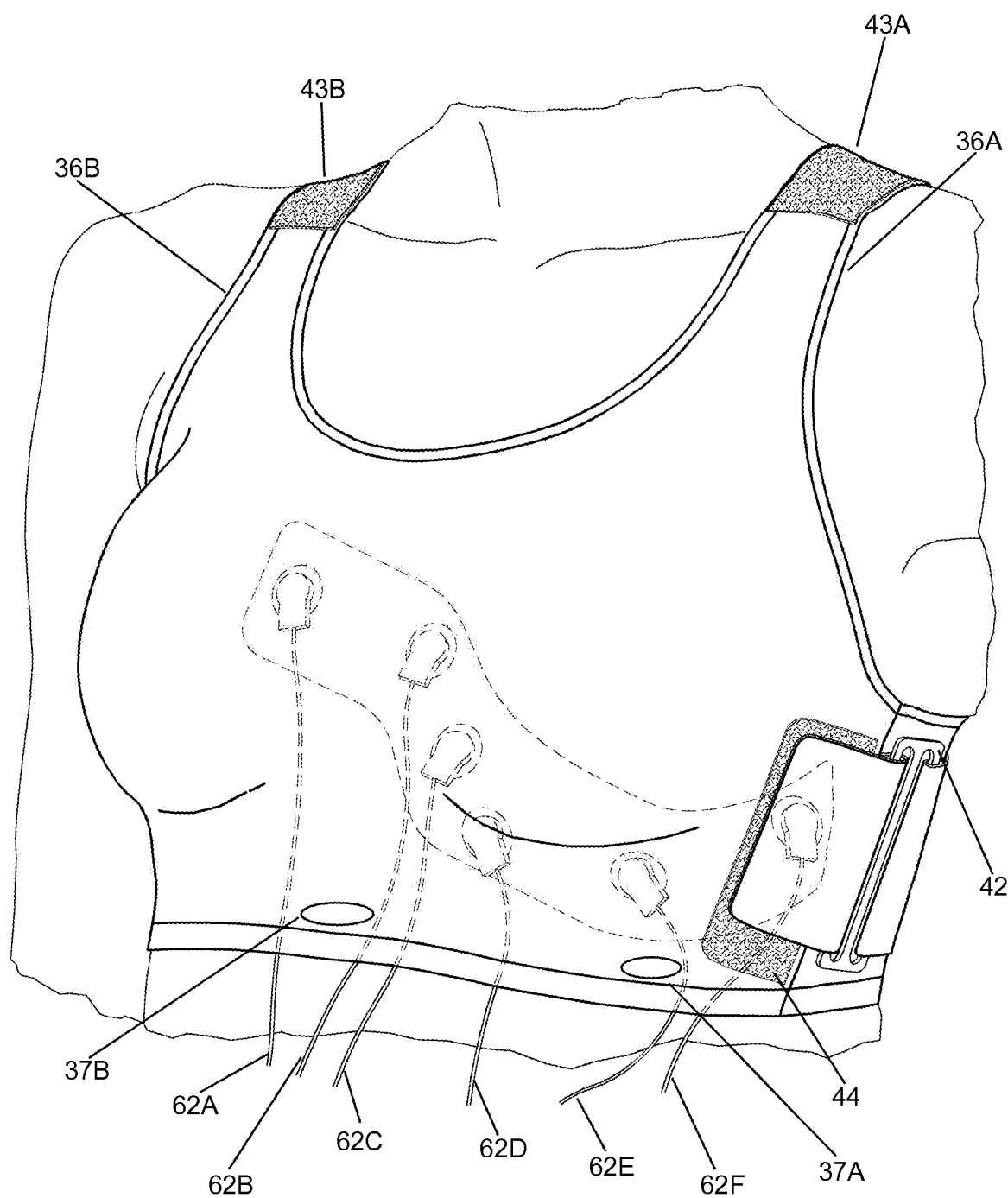
FIG. 8 is a view of an embodiment of the stress test garment with various attachment points.
Figure 9:
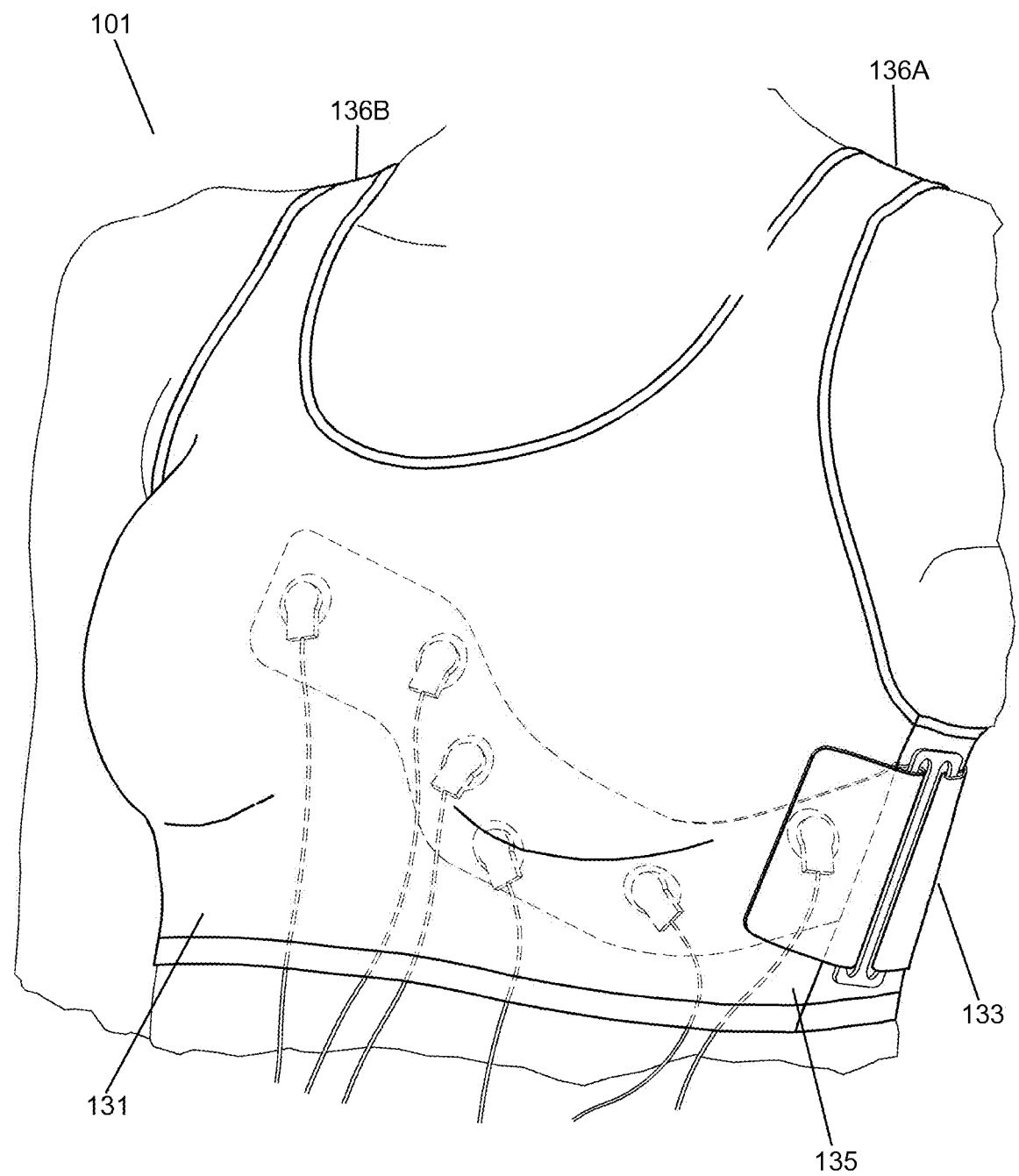
FIG. 9 is a view of the torso wearing an embodiment of the stress test garment.
Figure 10:
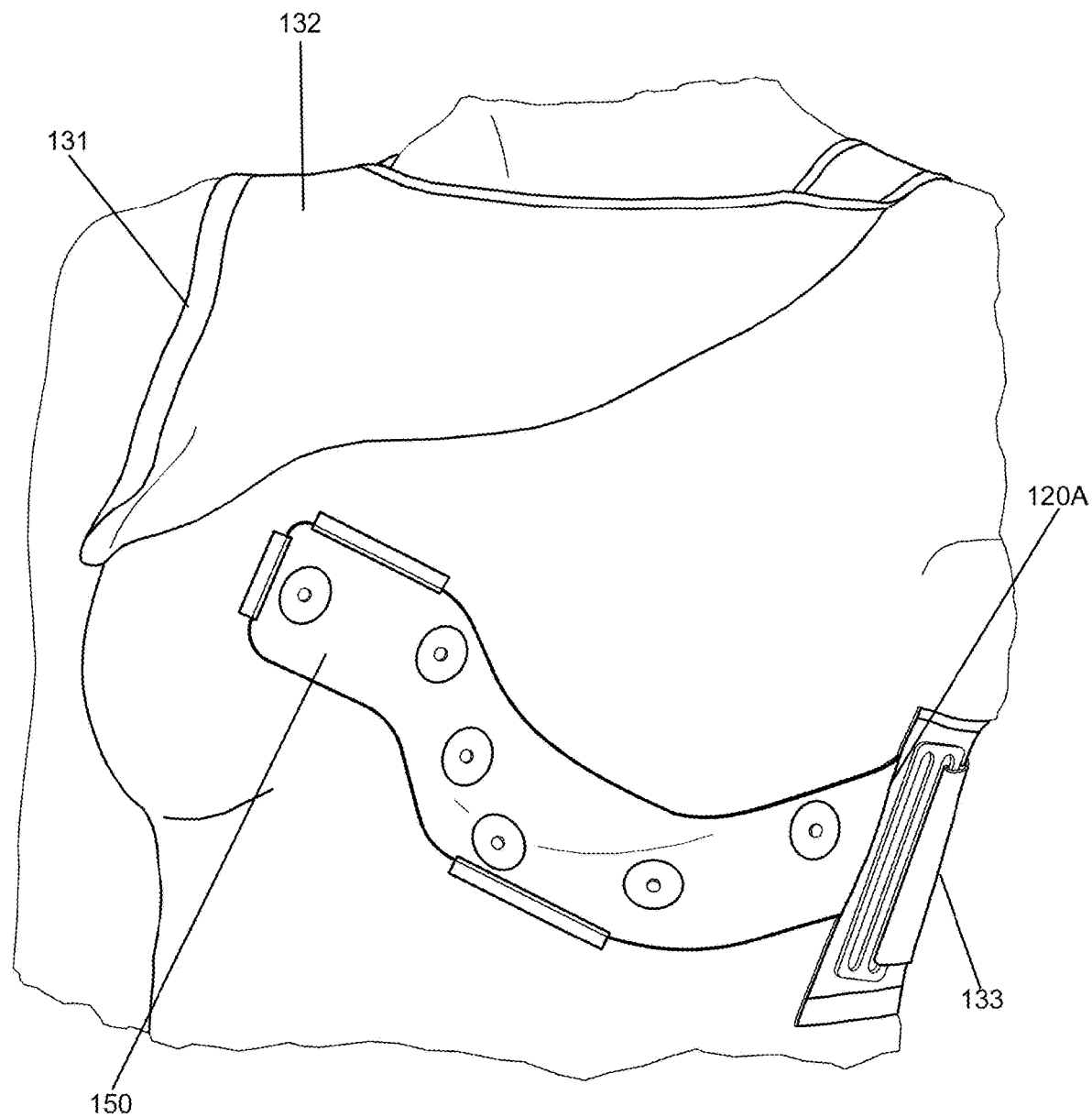
FIG. 10 is a view of an embodiment of the stress test garment with the support layer raised.

The first internal layer is the lead placement layer 10 and will include an inner surface 12 that is in communication with the skin of the user and an outer surface 14 that is in communication with support layer 30 of the garment 1. The support layer 30 (or second layer of the garment) also is configured with an inner surface 32 that is in communication with the outer surface of the lead placement layer 10 and an outer layer 34. The general configuration of the garment layers work together to ensure proper placement of the ECG leads on the user while still providing the support for a woman's breasts during the exercise portion of the stress test, but allowing for ease of access during imaging. The lead placement layer 10 may comprise six precordial ECG leads 52A-F. In some embodiments, the precordial ECG lead placement layer 10 may be in the form of a separate patch 50 or sticker configured to be placed on the lead placement layer 10. The patch 50 or sticker may also be placed directly on a patient's chest without using a lead placement layer 10. The precordial patch 50 or sticker may extend from the right $4^{th}$ intercostal space of a patient to the left mid-axillary space near the $5^{th}$ intercostal space of a patient, extending underneath the left breast. One of skill in the art will appreciate that the lead placement layer 10 may be placed on a patient's chest according to the type of measurements being made using the leads. As shown in FIGS. 9 and 10, in some embodiments, the patch 150, sticker or electrode lead placement layer 10 may be attached at the left mid-axillary space 120A to the support layer 130 to help minimize lead dislodgement and artifact. In some embodiments, the patch 150, sticker or electrode lead placement layer 110 may be removably attached to the support layer 130 so that the patch 150 can be detached from the support layer 130. In some embodiments, the lead placement layer 10 or patch 150 may be attached to the support layer 30, 130 at the right mid-axillary space 20B, 120B. The lead placement layer 10 and patch 50, 150 may also be attached to one or more straps 36A-B, 136A-B of the support layer 30, 130 at the right, left, or both shoulder (acromial) regions. The lead placement layer 10 and patch 50, 150 may be attached to the support layer 30, 130 at one or more of the right mid-axillary space 20B, 120B, the left mid-axillary space 20A, 120A, the first shoulder strap 36A, 136A of the support layer 30, 130, the second shoulder strap 36B, 36A of the support layer 30, 130, or combinations thereof. As shown in FIG. 7, the lead placement layer 10 may cover the entire breast of the patient. In this regard, the lead placement layer 10 may be connected to the support layer 30 so the assembly remains on the patient after detaching the first 33 and second ends 35 of the body panel of the support layer 30. Additionally, attaching the lead placement layer 10 to the support layer 30 at one or more locations helps ensure proper placement of the precordial patch 50. In another embodiment, the support layer 30 and lead placement layer 10 may include indicia 27A-B, 37A-B that allow for the layers to be aligned when in use to ensure proper placement on the patient. As shown in FIGS. 7-8, the indicia 27A-B, 37A-B are configured so when the ECG leads (either individual or as a precordial patch or multi-port ECG lead patch) are placed on the patient, the lead placement layer 10 and support layer 30 are then properly in place on the patient. The use of indicia 27A-B, 37A-B on the layers allows a user to more easily align the stress test garment 1 on the patient.

The lead placement layer 10 or first layer of the garment 1 is important for placing the ECG leads in the proper configuration on a user as well as then using the ECG leads during the stress test. In one embodiment, the electrodes may be incorporated into the first lead placement layer 10 so that the electrodes 52A-F are configured to contact and create communication with the patient's skin. In some embodiments, electrode leads 52A-F may be incorporated into a precordial patch 50 which may be placed on the lead placement layer 10. In embodiments where a precordial patch 50 is used with a second lead placement layer, the lead placement layer 10 may have one or more apertures or cut-outs that provide access to a patient's skin such that the electrodes contact and create communication with a patient's skin. The one or more aperture or cutout may be the same shape as the precordial patch 50. In other embodiments, the one or more apertures or cutouts may any shape and size necessary to accept one or more electrodes. Because the lead placement layer 10 may be used for ensuring proper placement of electrodes, or a precordial patch 50, the lead placement layer 10 may include indicia 24 that are indicative of appropriate lead placement or precordial patch 50 placement. Similarly, the support layer 30 may also include indicia indicative of appropriate lead placement. In an alternative embodiment, the lead placement layer 10 may also include a cut-out that is configured in the shape of the precordial patch 50 to ensure proper contact of the precordial patch 50 on the patient's skin as well as proper placement of the precordial patch 50 within the stress test garment 1. The cut-out portion, similar to the indicia 24, ensure proper placement by the person or healthcare professional of the precordial patch 50 for the desired testing.

The lead placement layer 10 may have a generally rectangular shape or shape similar to the support layer 30. The precordial patch 50 may also have a generally rectangular shape. The precordial patch 50 may also have an L shape or any shape to allow for proper placement on a user. The lead placement layer 10 may have a shape that allows the leads to be placed within the lead placement layer 10, wherein the leads align with the appropriate location when placed on a patient. In embodiments using a precordial patch, the patch 50 may have included electrodes 52A-F, or be configured to allow electrode leads to be placed within the precordial patch 50 such that the electrodes can contact and create communication with a patient's skin. One of skill in the art will appreciate that the lead placement layer 10 or precordial patch 50 may be any shape that allows for appropriate lead placement on a patient. In some embodiments, the system, lead placement layer 10, or precordial patch 50 may also include contact points for limb leads to be placed at the shoulder straps 36A-B of the support layer 30. One of skill in the art will appreciate that limb leads may also be separate from the lead placement layer 10 and the support layer 30. The limb leads may be standard button ECG lead sensors.

The lead placement layer 10, the precordial patch 50, or both may be formed from typical material known in the industry that is non-conductive material such as, but not limited to a plastic, cotton, polyvinyl chloride, polyethylene, or any other nonconductive material known in the art. One of skill in the art will appreciate the material used will be dependent on the desired imaging to be conducted. The lead placement layer 10, the precordial patch 50, or both may also be formed from a material that is radiolucent, allowing for imaging of the patient including x-raying or other types of nuclear imaging. The lead placement layer 10, the precordial patch 50, or both may range from substantially translucent to substantially transparent allowing for visualization of electrode placement when the second support layer 30 (or bra layer) is not obscuring a view of the lead placement layer 10. The inner surface 12, 54 of the lead placement layer 10 or the precordial patch 50 may have an adhesive applied in order to allow the lead placement layer 10 to stick to a patient's skin. The adhesive may be applied to the entire inner surface 12, 54 of the lead placement layer 10 or the precordial patch 50. In some embodiments, an adhesive may be applied to the perimeter of the inner surface 12 of the lead placement layer or the inner surface 54 of the precordial patch 50. The adhesive may be designed so the lead placement layer 10 or the precordial patch 50 can be easily removed from a patient's skin after use. In this regard, the adhesive may be any adhesive that allows atraumatic removal from the skin, is hypoallergenic, allows for removal and repositioning, and has excellent converting properties. In some embodiments the adhesive may be a 0.25 mm silicone gel adhesive coated onto the inner surface of the lead placement layer 10 or the precordial patch 50. One of skill in the art will appreciate that the silicone gel adhesive may have a thickness that is more or less than 0.25 mm. The electrodes attachments may be incorporated into the silicone gel adhesive patch. Because a patient may sweat while using the stress test garment 1, the adhesive applied to the inner surface of the lead placement layer 10 may be an adhesive that retains its adhesive attributes in the presence of liquids such as sweat. In some embodiments, the lead placement layer 10 or precordial patch 50 may be formed from a material that sticks to skin without the use of an adhesive. The lead placement layer 10 or precordial patch 50 may include a backing adhered to the inner surface. Similar to a sticker, the backing may be peeled away so the lead placement layer 10 or precordial patch 50 can be applied directly to a user's skin. The adhesive may be a silicone gel adhesive tape consisting of a silicone gel kin contact adhesive coated onto a polyurethane carrier. For example, the adhesive may be similar to Polymer Science PS-2056 and PS-1243. One of skill in the art will appreciate that the adhesive may be any biocompatible adhesive known in the art.

In one embodiment, the lead placement layer 10 is a single use layer that is removably connected to the frame of the stress test garment 1. In some embodiments, the lead placement layer 10 or a precordial patch 50 may be connected to the frame of the stress test garment 1 at one or more of the right mid-axillary space 20B, the left mid-axillary space 20A, the first shoulder strap 36A of the support layer 30, the second shoulder strap 36B of the support layer 30, or combinations thereof. The configuration of the support layer 30 and the lead placement layer 10 or the precordial patch 50 allows for a sonographer to open the support layer 30 quickly without dislodging the lead placement layer 10 or the precordial patch layer 50. With a single use design, the lead placement layer 10 or precordial patch 50 is connected to the skin of the patient to then allow for obtaining readings from the ECG. After the single use by the patient, the lead placement layer 10 or the precordial patch 50 may be removed from the patient and discarded. In some embodiments the placement layer 10 or the precordial patch 50 may be detached from the stress test frame or support layer 30 and discarded. In this regard, the lead placement layer 10 may be disposable. The electrode wires 62A-F may be reusable. In some embodiments the electrode wires 62A-F may be disposable. Similarly, the support layer 30 may also be single use or disposable. In alternative embodiments the lead placement layer 10 may be reusable and in such a configuration the lead placements will allow for reuse dependent on the specific design. In this alternative embodiment certain elements of the lead placements may only be a single use, such as any elements that connect to the skin of the patient.

The lead placement layer 10 is important for the design of the stress test garment 1 to allow for exercise stress testing and pharmaceutical stress testing to be run on the patient. To allow for the desired use, the lead placement layer 10 may have at least one conductive wire (or strip of wire) incorporated into the design. The wires may be attached to ECG sensors similar to wire attachments known in the art. While the wires 62A-F may be disposable, one of skill in the art will appreciate that the wires may be reusable. Each wire 62A-F may have a first end configured for contacting the patient's sensor which is in communication with the patient's skin so that an electrical connection is made with the patient's skin allowing an electrical signal to be relayed from the patient's skin to a second end of the wire. The first end of the conductive wire (or strip of wire) may be attached to the ECG lead sensor on the outer surface 14 of the lead placement layer 10. The wire may extend through the lead placement layer 10, exiting on the patient's left side or in an alternative embodiment on the right side. In an additional embodiment the stress test garment 1 may not include a lead placement layer 10 or this layer is configured by only a precordial patch 50 (multi-port ECG lead patch). The precordial patch 50 will be configured with at least one conductive wire (or strip of wire) incorporated into the design. The wires 62A-F may be attached to ECG sensors similar to wire attachments known in the art. While the wires may be disposable, one of skill in the art will appreciate that the wires may be reusable. Each wire 62A-F may have a first end configured for contacting the patient's sensor which is in communication with the patient's skin so that an electrical connection is made with the patient's skin allowing an electrical signal to be relayed from the patient's skin to a second end of the wire. The first end of the conductive wire (or strip of wire) may be attached to the ECG lead sensor on the outer surface 55 of the precordial patch 50. In another embodiment the precordial patch 50 will be configured to work in conjunction with the lead placement layer 10 due to the indicia 24 on the lead placement layer 10 or a cut-out section of the lead placement layer. In all configurations the fastener on the left side of the stress test garment 1 may be a tri-glide 42 may include an aperture for passing the wires through. The second end of the conductive wire may comprise a snap. The snap may be configured to be connected to a first end of a cable for relaying electrical signals from the patient to an ECG machine for monitoring of the user. Each wire 62A-F may exit out of the support layer 30 at the left mid axillary level. In some embodiments, the wires 62A-F may exit out of the support layer 30 along the bottom edge 46 of the body panel 31. In other embodiments, the wires 62A-F may exit out of the support layer 30 along the top edge 45 of the body panel 31. In some embodiments the snaps are formed from stainless steel. One of skill in the art will appreciate that the snaps may be formed from any conductive material known in the art. In one embodiment, the connection points may be located anywhere on the garment 1. In an optional embodiment, the connection points will be strategically located to allow for proper placement by the healthcare professional on the user. In a further optional embodiment, the connection points will be adjustable to allow for movement within the lead placement layer 10 of the garment 1. The snaps may be a commercially available snap such as a snap provided by Pepin Manufacturing, 3M, or Red Dot. One of skill in the art will appreciate that any type of snap used for ECG sensors may be used.

In one embodiment, the lead placement layer 10 or precordial patch 50 may include a plurality of sensors. The sensors may be selected from ECG sensors, body temperature sensors, heart rate sensors, or any other sensor known in the art. The sensors may be medical electrodes for collecting and measuring data related to the electrical system of the body. The sensors chosen will depend on the type of body functions selected to be measured. The type of electrode selected, and the placement of the electrode on the body, will determine the type of electrical activity measured. The type and use of sensors may be single use or multi-use sensors, these will be dependent on the attributes desired in the stress test garment 1. In some embodiments, the ECG sensors may be formed from a spunlace material.

The garment 1 and in particular the lead placement layer 10 or precordial patch 50 may include an ECG assembly that is compatible with existing or conventional ECG monitors. The ECG assembly generally comprises a plurality of ECG leads means for connecting the leads to an ECG monitor, and means for connecting the leads to the chest of a patient. The ECG assembly connects electrodes that are in contact with a patient's body for detecting electrical signal from the patient's body. In one embodiment for use with exercise electrocardiogram test there will be six precordial leads. The system may also include four limb leads configured to be attached to a patient's skin. It is envisioned the number of leads may vary depending on the analysis to be performed. In alternative embodiments the number of leads may be less than twelve leads. In an alternative embodiment the number of lead may be twelve leads, eleven leads, ten leads, nine leads, eight leads, seven leads, six leads or less. It is also envision the number of total leads used on a patient may vary and the stress test garment 1 may only include some of the leads to be affixed to the patient. One of skill in the art will appreciate that the number of leads may vary depending on the analysis to be performed. In one embodiment each lead will be configured to include a connecting wire from the lead to the ECG monitor. As an example if there are six leads then there will be six separate wires connecting the leads to the ECG monitor. In an alternative embodiment a single wire can connect each lead to each other with a single wire then connecting to the ECG monitor. In an additional alternative embodiment the leads may be configured as wireless leads that allow for the connection of the lead to the ECG in a wireless manner that allows for the transfer of information form the lead to the ECG monitor. Any method currently known in the industry for the relay of information from the lead to the ECG monitor can be used.

The leads or electrodes may be various types of leads used in the art. In some embodiments the leads may be gel electrodes that include a sensing element that transmits the electrical signal between the patient's skin and the sensing element using a conductive gel. In other embodiments the lead may be a dry electrode that does not requires gel for transmitting a signal. Leads may also include electrodes that are thin stickers. In some embodiments electrodes may be self-adhesive pads. The type of electrode used may vary depending on the duration of analysis. The electrode may consist of an electrically conductive electrolyte gel or foam and a silver/silver chloride conductor. A chloride gel or saline solution is used as a conductive bridge from the patient's skin to a silver/silver chloride sensor. The gel may also contain other compositions to permit electron conduction from the skin to the wire and to the electrocardiogram. In alternative embodiments the leads may only be lead attachments such as those used in 3M lead attachment (red dots). The use of only lead attachments incorporated into the lead placement layer 10 will allow for accurate placement of the leads onto the patient because of the incorporation into the lead placement layer 10. One of skill in the art will appreciate that dependent on the attachments means used to connect the lead to the patient such as with a gel that the gel may include potassium chloride, silver chloride or other compositions known in the art. In an alternative embodiment the garment 1 may also include the integration of ECG leads in the lead placement layers or precordial patch 50 that may be wireless and capable of wirelessly transmitting information to an ECG base station. Wireless capabilities may include radio transmission, Wi-Fi, or any other means of wirelessly transmitting data known in the art.

Figure 5:
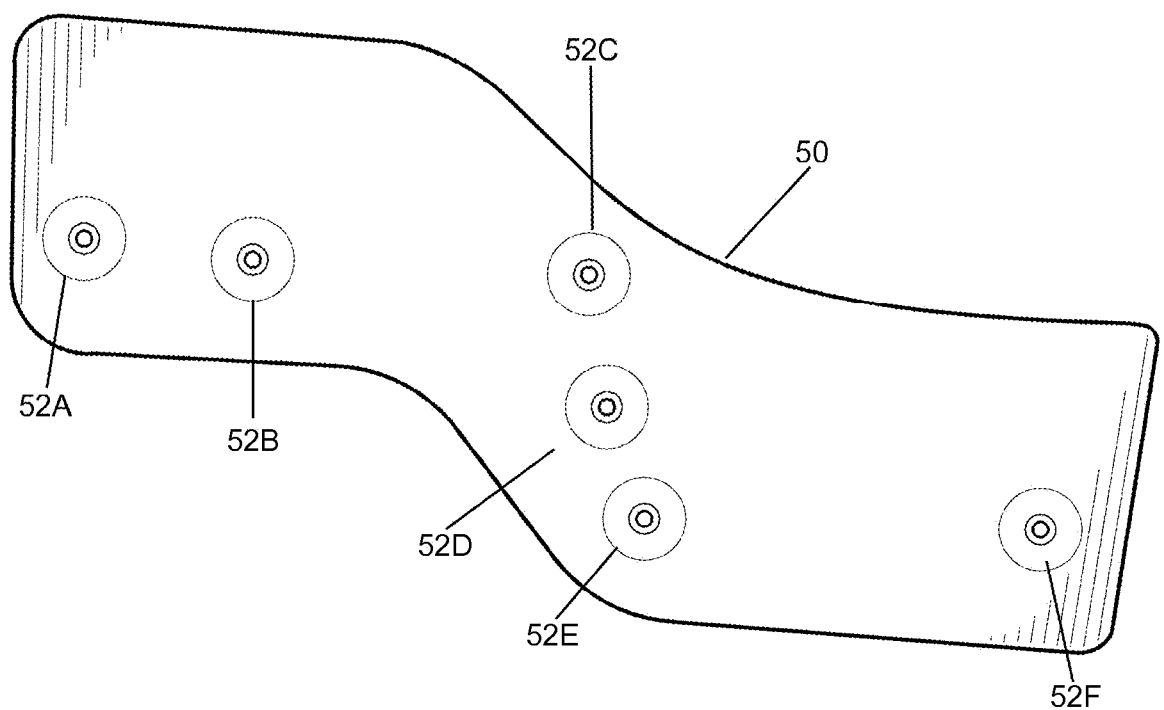
FIG. 5 is a view of the precordial patch.
Figure 6:
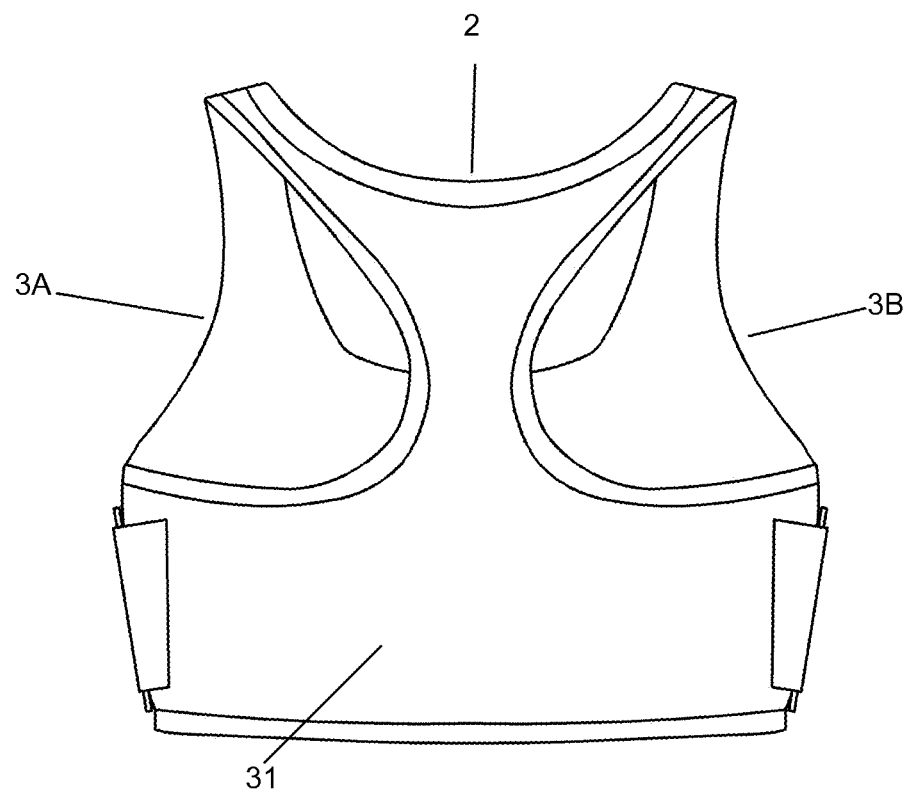
FIG. 6 is a view of an embodiment of the stress test garment with a support layer that has two closures.
Figure 11:
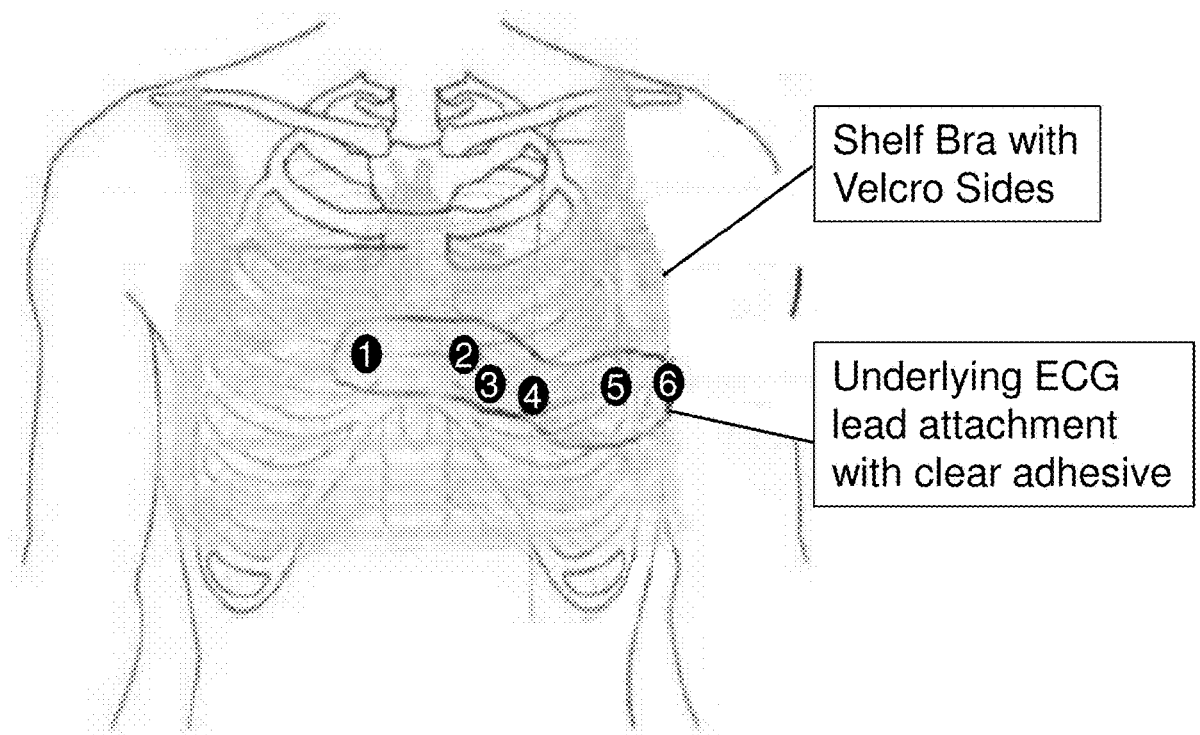
FIG. 11 is a view of the torso with a chest electrode placement guide.
Figure 12:
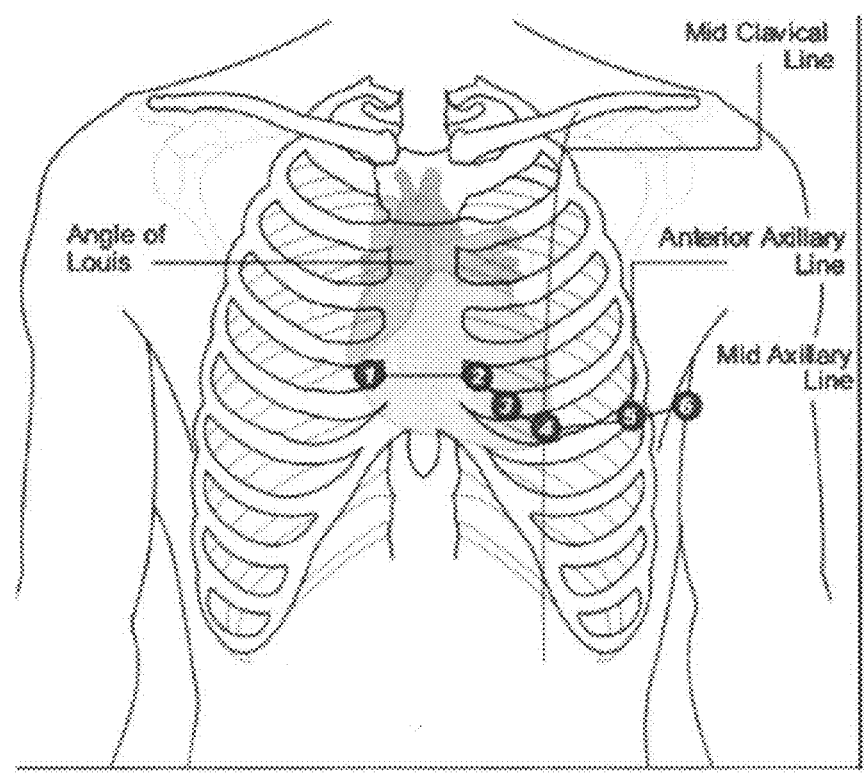
FIG. 12 is a view of the torso with a chest electrode placement guide.

FIGS. 11 and 12 show the standard lead ECG requires ten electrodes including six chest electrodes are placed on the following locations: V1, in the fourth intercostal space (between ribs 4 and 5) just to the right of the sternum (breastbone); V2, in the fourth intercostal space (between ribs 4 and 5) just to the left of the sternum; V3, midway between V2 and V4; V4, in the fifth intercostal space (between ribs 5 and 6) in the mid-clavicular line; V5, horizontally even with V4, in the left anterior axillary line, or midway between V4 and V6; and V6, horizontally even with V4 and V5 in the mid-axillary line. The four limb electrodes may be placed on the following locations: LA, left arm; RA, right arm; N, on the right leg; F, on the foot. In various embodiments the lead placement layer 10 or precordial patch 50 may include various configurations of the chest electrodes. As demonstrated in FIG. 5 the precordial patch 50 includes leads that are positioned similar to the lead ECG placement standards. Because improper lead placement may lead to artifacts in the ECG reading, the lead placement layer 10 of the garment 1 provides various means for assuring proper lead placement. In one embodiment the placement configuration of the electrodes within the lead placement layer 10 ensure proper placement when the user wears the garment 1. In another embodiment the indicia 24 on the lead layer or cut-out of the lead layer will correspond to the precordial patch 50 to ensure proper placement when the user wears the garment 1 with the precordial patch 50. The garment 1 will ensure proper placement of the lead electrodes by enabling contact directly beneath breast tissue and providing support by the elastic garment overlay or second support layer that overlays the electrodes to ensure adequate contact. The electrode layer will have different ranges of sizes of electrode placement based on thoracic/chest circumference. The sizes and placement of the lead will be configured based on the following: The electrode/lead layer of the garment 1 in conjunction with the support layer will ensure appropriate and rapid lead placement on a patient. The lead placement layer 10 may be adjusted to the patient based on the patient's thoracic circumference. By way of non-limiting example, the precordial patch may be formed using the following algorithm:

¼ Thoracic circumference (t)+5 inches=width (w) of layer 1
V1 lead placement is ½ inch from left side of layer 1.
V2 lead is 4 inches to the right of V1
V3 lead is halfway between V2 and V4
V4 lead ⅛ inch from the left side 4 inches below V2
V5 lead halfway between V6 and V4 at the same horizontal level
V6 lead placement is ½ inch from the right side of layer 1

The electrode/lead placement layer 10 of the garment 1 in conjunction with the support layer will ensure appropriate and rapid lead placement on a patient. The thoracic circumference of the patient may be estimated using the patient's bra size. The thoracic circumference of patient is 4-5 inches smaller than the bra size. The patient's bra size and cup size may be used to determine sizing of the support layer.

By way of non-limiting example, a patient that has a 36 C bra, may have a thoracic circumference that is approximately 31-32 inches. Further, the circumference of the chest at the largest point of the breast is approximately 39 inches. A patient with a thoracic circumference of 32 inches may have a precordial patch width of (¼ thoracic circumference+5 inches) 13 inches and a length of approximately 6 inches. As another non-limiting example, a patient that is a 36 C bra size would be a size Medium bra size for the support layer. In many embodiments, because sizes are based on thoracic circumference, the support layer and the lead placement layer 10 or precordial will have sizes that correspond to one another and may be the same. In cases of a mastectomy or other disproportionate sizing, the layers may be combined in any combination that best suits the patient. The following chart describes the relationship between bra band size and thoracic circumference.

| RIB CAGE/Thoracic circumference | BRA BAND SIZE |
|---|---|
| 25"-27" | 30 |
| 27"-29" | 32 |
| 29"-31" | 34 |
| 31"-33" | 36 |
| 33"-35" | 38 |
| 35"-37" | 40 |
| 37"-39" | 42 |
| 39"-41" | 44 |

As a non-limiting example, the support layer size may be chosen using the following chart:

|   | 28 | 30 | 32 | 34 | 36 | 38 | 40 | 42 | 44 |
|---|---|---|---|---|---|---|---|---|---|
| A | XS | XS | XS | S | M | L | XL | XXL | XXL |
| B | XS | S | S | M | M | L | XL | XXL | XXL |
| C | S | S | M | M | L | L | XL | XXL | XXL |
| D | M | M | M | M/L | L | XL | XXL | XXL | XXL |
| E | L | L | L | L | XL | XXL | XXL | XXL | XXL |

-continued

| 28 | 30 | 32 | 34 | 36 | 38 | 40 | 42 | 44 |
|----|----|----|----|----|----|----|----|----|
| F  | L  | XL | XL XL | XL | XXL | XXL | XXL | XXL |

The support layer of the garment 1 is configured to perform functions similar to traditional bras ensuring support for the user. In one embodiment, the support layer acts as a sports bra or support bra. As such, the support layer may be formed from stretch fabrics such as spandex, elastane, cotton, polyamide, or combinations thereof. One of skill in the art will appreciate that any materials known for forming a sport bra may be used that will help support the breasts, especially during exercise activity. The support layer 30 may be configured to wick moisture, including sweat, away from the patient. In a closed configuration, where the support layer is secured to the lead placement layer 10, the support layer 30 may provide breast support that is similar to a traditional sports bra, namely by compression and elevation of the breasts so that exercise does not cause discomfort as well as minimizing movement of the breasts. In optional embodiments, both the lead layer 10 and the support layer 30 (second layer or second support layer) provide support to the user's breast.

The garment 1 may include one or more straps 16A-B that are configured within the support layer 30 and can work in conjunction with the lead placement layer 10. The straps 16A-B may be configured to provide support for the brassiere from the wearer's shoulders or around the neck such as in a racer back shape around the neck. In some embodiments the straps 16A-B may have a first end and a second end, wherein each end is connected to the body panel 31 of the garment 1. The first end of the strap may be connected to the front of the body portion 31 and the second end may be connected to the rear of the body portion 31 forming an armhole 3A-B and a neck hole 2 for the user. The one or more straps 16A-B may be fixedly attached to a surface of the body portion 31. The straps 16A-B may be removably attached to the body portion 31 using various attachment members known in the art, including, but not limited to snaps, buckles, buttons, or zippers, hook and eye fasteners, tri-glides, or hook and loop fasteners. In some embodiments, the straps 16A-B are attached to the top edge 45 of the body portion 31. The straps 16A-B may also be attached to the bottom edge 46 of the body portion 31. One of skill in the art will appreciate that the straps 16A-B may be attached to any part of the body portion 31 so that the straps 16A-B provide support from the user's shoulders or optionally around the user's neck. The straps 16A-B may be adjustable using buckles or other adjustable members known in the art for adjusting bra straps 16A-B or other similar garments.

The body portion of the garment 1 may have a plurality of panels that are easily detached from one another for quick removal of the garment 1 or adjustment for the user's comfort. Similarly, the straps 16A-B of the bra may be configured for quick removal. In some embodiments, the garment 1 may have fasteners that aid in quick removal. The ends of the body portion may be attached under one or both armholes. In one embodiment, the body portion of the support layer is configured with the fastener system on the left side of the user under the left arm of the user. In this embodiment the fastener is designed to allow for the ease of use of connecting the base to create a complete circumference around the user. The configuration of the support layer 30 with the fastener 42 further allows for the ease in unfastening to then allowing for the support layer 30 to be moved from the visual area where the heart will be imaged. In alternative embodiments, the fastener 42 can be configured under the right arm of the user, which may be used for patients with dextrocardia. In some embodiments, the fastener 42 can be configured under both the right and left arm of the user. The body portion 31 may have a first end 33 and a second end 35. In some embodiments, the first 33 and second ends 35 of the body portion 31 are attached at the center rear of the body portion. In some embodiments, the first 33 and second ends 35 of the body portion are attached at the center front of the body portion. The first 33 and second ends 35 of the body portion may be attached using hook and loop fasteners such as Velcro, tri-glide as well as any other attachment members known in the art, and combinations thereof. In embodiments using a tri-glide, the tri-glide may be used along with hook and loop fasteners to secure free ends of the body portion to keep the garment 1 in a support configuration that may be worn while a patient exercises as shown in FIG. 8. The size of the body portion 31 and the stress test garment 1 overall will be configured based on current industry standards for the size standard for bras or other garment products. As an example the stress test garment 1 can be a size 26, 28, 30, 32, 34, 36, 38, 40, 42, 48, 50, 52, 54, and larger dependent on the patient. One of skill in the art will appreciate the size will be within a desired range.

The front panels of the garment 1 may form cups for accepting and supporting a user's breast(s). The cups are configured to provide support and may be the same size as one another or may have different sizes to accommodate a user having breasts of different sizes. The cups may have a triangular shape that narrows as it meets the strap. One of skill in the art will appreciate that the cups may be any shape known in the art that creates the support desired by a user. This cup size can be a range or a single size as currently used in the industry. The cup size can be AA, A, B, C, D, DD/E, DDD/F, or G.

The garment 1 may have a configuration that includes a frame with a first and a second bra cup removably attached to the frame. The garment frame may have a generally traditional bra shape. The frame may include shoulder straps 16A-B for supporting the frame on the user's shoulders. The frame may include a neck strap for supporting the frame with the user's neck. The frame may also have a body portion where the front of the frame has openings for accepting the breast of the user. In some embodiments the front of the frame has one opening for accepting two breasts. The one or more openings are generally sized to accommodate breasts there through so that the frame is around the sides of the breasts. The garment 1 may have cups removably attached to the frame. The cups may be interchangeable so they can be removed and replaced without keeping track of which cup should be coupled to the bra frame. One of skill in the art will appreciate that the second support layer may not include a frame.

The lead placement layer 10 and support layer 30 are configured to create the complete garment 1 that will provide support for the user during movement such as exercise during the stress test by the user. Additionally, the support layer is configured to be removed from communication with the lead placement layer 10 to then allow for imaging of the user. The separation of the support layer and lead placement layer 10 is important to allow for the imagining of the user. The support layer is removed from the area of the patient to be imaged. In one embodiment, the support layer will include removable attachment members that allow for the support layer to disengage from the lead placement layer 10.

In another embodiment, the lead placement layer 10 can include a frame that is configured with openings creating a perimeter that encircles a user's breasts. The garment 1, having a frame with openings, forms window like apertures wherein the lead placement layer 10 acts as a transparent layer that allows for visualization of the breast or breasts that are covered by the lead placement layer 10. The support layer 30 may also include a mechanism that allows for the connection of the bottom part of the support layer to the upper strap section of the support layer. This connection mechanism will allow for the support layer 30 to still communicate with the user, but the support layer 30 allows for the visualization of the breast to ensure good imaging results since the support layer will then not impair the visual field for the imaging machine. In one embodiment the straps 36A-B of the support layer 30 can include a section 43A-B of hook and loop that will allow for the hook and loop to connect with the bottom section of the support layer to further hold the support layer out of the visual field of the user's heart will be imaged. In a further embodiment any mechanism known in the art for connecting the bottom section of the support layer to the upper section of the support layer can be used that allows for holding the support layer 30 out of the visual field of the users heart. In frameless embodiments, the first 33 and second ends 35 of the body portion 31 of the support layer 30 may be detached from one another to allow for the visualization of the breast. In frameless embodiments, the first or second end of the body portion 31 of the support layer 30 may be held out of the way by attaching one or both ends of the body portion to the shoulder attachment area 43A-B of one or both of the straps 16A-B as shown in FIG. 8.

The support layer 30 may be removably attached to the frame at various points around the support layer 30. In one embodiment the support layer 30 is removably attached to the frame along the entire perimeter of the support layer and the one or more frame openings. In an optional embodiment, the support layer 30 may be fixedly attached to the frame along a bottom edge of the support layer 30 and removably attached at various other points along the perimeter of the support layer so that when detached, the support layer 30 or a portion of the support layer, forms one or more panels that hang down exposing the lead placement layer 10 and allows for imaging of the user. In an optional embodiment, the support layer 30 may be fixedly attached to the frame along an edge that then allows for the support layer to be detached from the side portion of the lead placement layer 10 or the midpoint of the lead placement layer 10 near the sternum of the user to remove the support layer from the visual field when an image of the user is desired. In an optional embodiment, the support layer is fixedly attached to the strap or neck portion of the garment 1 and removably attached along the perimeter of the frame. In a further optional embodiment the support layer may connect to the mid sternal and superior margin of the frame of the stress test garment 1. The various removable attachments may include various attachment members known in the art, including but not limited to snaps, buckles, buttons, zippers, hook and eye fasteners, hook and loop fasteners or combinations of the above. The configuration of the lead placement layer 10 and support layer work together to create a garment 1 that allows for ease in proper placement of ECG leads, providing support for a user during the exercise portion of a stress test, and finally allows for the removal of the support layer when an image is taken of the user, immediately following the exercise portion of the stress test.

Because the garment 1 may be used on patient's who require x-ray imaging, nuclear imaging, or echocardiography exams, the garment 1 may be radiolucent and echolucent. Accordingly, the components of the garment 1 and the electrodes or sensor used with the garment assembly 1 are constructed of radiolucent materials. One of skill in the art will appreciate that radiolucent electrodes are known in the art and may be purchased from companies such as 3M and Medtronic.

Method:

The system may be used by first determining the appropriate size of the support layer, the lead placement layer 10, and the precordial patch using a size selection chart. Next, the patient may undergo an initial resting echocardiogram without wearing the stress test garment 1. After resting echo images are obtained, the lead placement layer 10 with the precordial patch may be applied to the patient along with the appropriate electrode wires. The support layer may then be secured to the patient according to the patient's comfort.

The patient may then be connected to an ECG machine and placed on a treadmill. Next, the patient may exercise using a Bruce protocol study. As required by the exercise stress echocardiogram protocol, the sonographer may begin imaging after exercise. Prior to imaging, a sonographer or other appropriate technician may open the support layer from the left side to allow for image acquisition. The electrode layer (lead placement layer and/or precordial patch) may remain in place during imaging. After the post-stress images are obtained, the electrode wires may be detached and the patient may remove the lead support layer.

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A garment assembly for use with exercise stress electrocardiogram comprising:
   a lead placement layer, wherein the lead placement layer includes electrocardiograph electrodes placed within the lead placement layer, and the lead placement layer and electrocardiograph electrodes are configured to contact and connect to the skin of a patient without support from another layer, the lead placement layer further includes indicia to identify and allow placement of the electrocardiograph electrodes on a patient;
   a support layer, wherein the support layer has a form of a sports bra, the support layer further includes a body portion, with the body portion having a first end and a second end that are detachedly affixed to one another, the body portion includes a fastener system to connect the first end and the second end, the fastener system is configured under either a left arm hole or a right arm hole of the sports bra, to allow for rapid release for clinical use for imaging of the patient;

the garment assembly further includes at least one strap, with the support layer including a fastener to removably attach the support layer to the strap;

the lead placement layer is configured to attach to the at least one strap and remain attached to the at least one strap when the support layer is disengaged from the strap; and an array of electrocardiograph electrodes for use with electrocardiograph analysis;

wherein the support layer is configured to be removed from communication with the lead placement layer, with the lead placement layer and electrocardiograph electrodes remaining in contact and connection with the skin of the patient when the support layer is removed, to allow for imaging of a user, whereby in use the support layer is removed from the area of the patient to be imaged.

2. The assembly of claim 1, wherein the first end and the second end are detachedly affixed with the fastener system, wherein the fastener system is selected from the group consisting of a tri-glide fastener, a hook and loop fastener or combinations thereof, further the fastener system includes an aperture for passing wires through.

3. The assembly of claim 1, wherein one or more of the lead placement layer, the support layer, and the array of electrocardiographic electrodes are composed from radiolucent materials.

4. The assembly of claim 1, wherein one or more of the lead placement layer, the support layer, and the array of electrocardiographic electrodes are composed from echolucent materials.

5. The assembly of claim 1, wherein the support layer further includes—a first and a second bra cup removeably attached to the shoulder straps of the support layer, to allow for adjustment of the electrocardiograph electrodes in the lead placement layer.

6. The assembly of claim 1, wherein the lead placement layer has an inner surface and an outer surface, wherein the inner surface is configured to be removably attached to the skin of a patient.

7. The assembly of claim 1, wherein the support layer is configured to wick sweat away from a patient.

8. The assembly of claim 1, wherein the lead placement layer includes an adhesive, wherein the adhesive retains its adhesive attributes in presence of sweat or other liquids.

9. The assembly of claim 1, wherein the garment assembly includes two straps, and wherein the two straps both include a fastener configured for removably attaching the support layer to the two straps, wherein the fastener is selected from the group consisting of a snap, buckles, buttons, hook and eye fasteners, hook and loop fasteners or combinations thereof.

10. The assembly of claim 1 further comprising a precordial electrocardiogram (ECG) patch or 10 lead electrodes.

11. The assembly of claim 1, wherein the lead placement layer is a precordial patch or electrode layer.

12. The assembly of claim 1, wherein the lead placement layer includes a first layer in communication with the support layer, and a second layer that is a precordial patch or electrode layer, wherein the first layer of the lead placement layer includes indicia for placing the precordial patch.

13. A method of using a bra having an array of electrocardiograph electrodes comprising:

measuring the chest size of a patient;

choosing a lead placement layer that corresponds to the chest size of the patient, wherein the lead placement layer includes electrocardiograph electrodes placed within the lead placement layer, the lead placement layer further includes indicia to allow for placement of electrocardiograph electrodes on a patient;

choosing a support layer that corresponds to the chest size of the patient, wherein the support layer has a form of a sports bra, the support layer further includes a body portion, with the body portion having a first end and a second end that are detachedly affixed to one another, the body portion includes a fastener system to connect the first end and the second end, the fastener system is configured under either a left arm hole or a right arm hole of the sports bra; the sport bra further includes at least one strap, with the support layer including a fastener to removably attach the support layer to the strap, the support layer further includes a first bra cup removeably attached to the strap; and wherein the support layer is configured to be removed from communication with the lead placement layer, while the electrocardiograph electrodes remain connected to the patient, whereby the support layer is removed from the area of the patient to be imaged to allow for imaging of a patient;

placing the lead placement layer on the patient, using the indicia to allow for the proper placement of the electrocardiograph leads on the patient;

connecting the lead placement layer to an electrocardiograph monitor;

placing the support layer on the patient;

conducting a stress test electrocardiogram test to monitor the patient, while the patient is on a treadmill, after the exercise the support layer is removed from communication with the lead placement layer to allow for imaging of the patient, allowing the electrocardiographs electrodes to remain in place during the image acquisition to continue to collect information;

disconnecting the electrocardiograph monitor; and removing the garment.

14. The method of claim 13, further including the step of connecting the support layer to a strap of the bra.

15. The method of claim 14, wherein the lead placement layer is a precordial patch or electrode layer.

* * * * *